United States Patent
Jordan

(10) Patent No.: US 11,648,096 B2
(45) Date of Patent: May 16, 2023

(54) METHOD FOR THE COMPUTER-AIDED EDITING OF A DIGITAL 3D MODEL

(71) Applicant: SIRONA DENTAL SYSTEMS GMBH, Bensheim (DE)

(72) Inventor: Thorsten Jordan, Pfungstadt (DE)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 15/300,114

(22) PCT Filed: Feb. 4, 2015

(86) PCT No.: PCT/EP2015/052230
§ 371 (c)(1),
(2) Date: Sep. 28, 2016

(87) PCT Pub. No.: WO2015/117973
PCT Pub. Date: Aug. 13, 2015

(65) Prior Publication Data
US 2017/0181816 A1    Jun. 29, 2017

(30) Foreign Application Priority Data

Feb. 4, 2014   (DE) ..................... 10 2014 201 993.1

(51) Int. Cl.
*A61C 13/00*     (2006.01)
*G06T 19/20*     (2011.01)
(Continued)

(52) U.S. Cl.
CPC .......... *A61C 13/0004* (2013.01); *A61C 13/34* (2013.01); *G06F 30/00* (2020.01); *G06T 19/20* (2013.01); *G16H 20/40* (2018.01)

(58) Field of Classification Search
None
See application file for complete search history.

(56) References Cited

U.S. PATENT DOCUMENTS 7,821,513 B2 *  10/2010  Bae ........................ G06F 17/50
                                                        345/419
7,974,721 B2    7/2011   Shibata
                         (Continued)

OTHER PUBLICATIONS

Sirona, "CEREC SW Operator's Manual Software Version 4.0", Jul. 2011, Sirona Denal Systems GmbH.*
(Continued)

*Primary Examiner* — Robert Bader
(74) *Attorney, Agent, or Firm* — Dentsply Sirona Inc.

(57) ABSTRACT

A method for the computer-aided editing of a digital 3D model (1) of a dental object using digital tools (T1, T2, T3) provides for the identification of different dental-specific regions (R1, R2, R3) of the 3D model (1) that are affected by the tool (T1, T2, T3) in different ways, for computation of the effect on the whole 3D model and for display thereof as a proposal model (2) together with the 3D model (1). The proposal model (2) is then rejected or accepted in part or in full. If it is accepted in part, at least one subregion of the 3D model (1) is selected as a region (10) and a result model (6) is formed from the 3D model (1) and the proposal model (2) by virtue of the 3D model (1) being taken as the starting point for replacing the selected region (10) or at least a central portion of the selected region (10) with a corresponding region of the proposal model (2) or approaching the latter using a strength factor (S).

19 Claims, 1 Drawing Sheet

(51) Int. Cl.
  *A61C 13/34* (2006.01)
  *G06F 30/00* (2020.01)
  *G16H 20/40* (2018.01)

(56) References Cited

U.S. PATENT DOCUMENTS

| 8,594,820 | B2 | | 11/2013 | Manai | |
|---|---|---|---|---|---|
| 9,396,291 | B2 | * | 7/2016 | Meier | A61C 13/0004 |
| 2006/0155404 | A1 | * | 7/2006 | Hanisch | A61C 13/0004 |
| | | | | | 700/98 |
| 2013/0179126 | A1 | * | 7/2013 | Meier | A61C 13/0004 |
| | | | | | 703/1 |

OTHER PUBLICATIONS

Rafael Bidarra, Alex Noort, Daniel Lourenco, Pedro Oliveira, "Advanced Direct Manipulation of Feature Models", Mar. 2007, Proceedings of the 2nd International Conference on Computer Graphics Theory and Applications—GRAPP 07, pp. 130-136.*

Wei Zhao, Shuming Gao, Yusheng Liu, Hongwei Lin, "Poisson based reuse of freeform features with NURBS representation", Jan. 2009, Elsevier, Computers in Industry, vol. 60, Issue 1, pp. 64-74.*

Yokesh Kumar, Ravi Janardan, Brent Larson, "Automatic Feature Identification in Dental Meshes", 2012, CAD Solutions, LLC, Computer-Aided Design & Applications, 9(6), 747-769.*

Mark Meyer, Mathieu Desbrun, Peter Schroder, Alan H. Barr, "Discrete Differential-Geometry Operators for Triangulated 2-Manifolds", 2003, Springer, Visualization and Mathematics III pp. 35-57.*

Hong-Tzong Yau, Chien-Yu Hsu, Hui-Lang Peng, Chih-Chuan Pai, "Computer-aided Framework Design for Digital Dentistry", 2008, CAD Solutions, LLC, Computer-Aided Design and Applications, 5(5), pp. 667-675.*

Karol Mys:zlcowski, Vladimir V. Savchenko, Tosiyasu L. Kunii, "Computer modeling for the occlusal surface of teeth", Jun. 28, 1996, IEEE, Proceedings of CG International '96, pp. 191-197.*

Shu-Xian Zheng, Jia Li, Qing-Feng Sun, "A novel 3D morphing approach for tooth occlusal surface reconstruction", Mar. 2011, Elsevier, Computer-Aided Design, vol. 43, Issue 3, pp. 293-302.*

T. Hayashi, J. Tsuchida, and K. Kato, "Semi-Automatic Design of Tooth Crown Using a 3-D Dental CAD System, Vocs-1B", Jul. 28, 2000, IEEE, Proceedings of the 22nd Annual International Conference of the IEEE Engineering in Medicine and Biology Society, pp. 565-566.*

Miguel Vieira, Kenji Shimada, "Surface mesh segmentation and smooth surface extraction through region growing", Nov. 2005, Elsevier, Computer Aided Geometric Design, vol. 22, Issue 8, pp. 771-792.*

Manfred Lau, Jinxiang Chai, Ying-Qing Xu, Heung-Yeung Shum, "Face Poser: Interactive Modeling of 3D Facial Expressions Using Facial Priors", Dec. 15, 2009, ACM, ACM Transactions on Graphics, vol. 29, Issue 1, Article No. 3.*

V. Blanz, A. Mehl, T. Vetter, H.-P. Seidel, "A Statistical Method for Robust 3D Surface Reconstruction from Sparse Data", Sep. 9, 2004, IEEE, Proceedings. 2nd International Symposium on 3D Data Processing, Visualization and Transmission, 2004 (3DPVT 2004).*

* cited by examiner

METHOD FOR THE COMPUTER-AIDED EDITING OF A DIGITAL 3D MODEL

CROSS-REFERENCE TO RELATED APPLICATIONS

This is a National Phase application of International Application No. PCT/EP2015/052230, filed Feb. 4, 2015, which claims the benefit of and priority to German Application Ser. No. 102014201993.1, filed on Feb. 4, 2014, which are herein incorporated by reference for all purposes.

TECHNICAL FIELD

The invention relates to a method for the computer-aided editing of a digital 3D model of a dental object using digital tools. For this purpose, at least one digital tool is selected and an effect of the tool is computed for the whole 3D model.

BACKGROUND OF THE INVENTION

In computer-aided editing of 3D models, in particular of teeth, tools are used that change the shape of the 3D model. For example, the tools always affect the whole 3D model or only regions of the 3D model selectable manually using input devices, such as parts that are reasonable from a dental technology point of view.

In doing so, the exact effect of the tool cannot be precisely predicted by the user so that often it cannot be assessed until after the tool is applied whether the result is useful. If the result is not useful, the changes must be undone again or corrected by using other tools.

Such editing requires considerable experience regarding the effect of the tools in order to achieve results as useful and as quickly as possible. The manual selection of regions or the limitation of the effect of the tool in a manner that is reasonable from a dental technology point of view requires experience of the user.

The task of this invention is to provide a method, which ensures due consideration of dental technology criteria and also allows an inexperienced user to estimate the effect of a tool on a 3D model of a dental object.

SUMMARY OF THE INVENTION

This task is solved by a method for the computer-aided editing of a digital 3D model of a dental object using digital tools, wherein at least one digital tool is selected and an effect of the tool is computed for the whole 3D model. In the process, different regions of the 3D model are identified, wherein at least one region corresponds at least in part to an occlusal or incisal or labial or buccal or distal or mesial or lingual or palatal surface of the dental object and wherein the tool affects the different regions differently. The effect computed for the whole 3D model is provided as a proposal model and displayed together with the unchanged 3D model. Subsequently, the proposal model is rejected or accepted in part or in full. If it is accepted in full, the proposal model is displayed as a result model. If it is accepted in part, the whole 3D model or at least a region or at least a subregion of the 3D model is selected as region. From the 3D model and the proposal model, a result model is formed by virtue of the 3D model being taken as the starting point for replacing the at least one selected region or at least a central portion of the selected region with a corresponding region of the proposal model or approaching the latter using at least one strength factor, wherein the result model is displayed.

This method ensures that the effect of a tool is limited to parts of the 3D model that are reasonable from a dental technology point of view and furthermore allows a user to view this possible effect of the tool in comparison to the 3D model, to let the tool only have a partial effect and to return to the original 3D model in full or in part at any time.

A dental object, i.e. one or several teeth or a tooth restoration, comprises different regions or surfaces. These are one lower side or one tooth root region as well as five surface regions, which point in different directions and whose specific dental notation depends on the orientation and position of the dental object in the jaw. For example, a molar tooth has a chewing surface, i.e. an occlusal surface, as well as lateral surfaces, mesially, distally, buccally and lingually or palatally. The occlusal surface also has indentations or fissures as well as cusps. An incisor has an incisal surface or edge as chewing surface and also lateral surfaces, which are denoted as mesial, distal, labial and lingual or palatal.

At least one specific dental region is identified in accordance with the invention. The identification of these different typical dental regions or at least of one of these regions allows for varying the effect of the tool according to dental technology criteria, such as limitation to certain regions and/or the strengthening toward the center of a region.

It can, for example, be ensured that a tool for adapting to a neighboring tooth essentially affects the mesial and/or distal surface or even, in particular, strengthens the effect on a central region of this surface and that the adjacent regions, such as the lingual surface or the incisal or occlusal surface, are only adapted to the changes of the mesial and/or distal surface to the extent that this is necessary. The effect of a tool to create points of contact to an opposite tooth can, however, remain limited to the incisal or occlusal surface or even to the cusps of the occlusal surface, for instance.

Using a suitable input device, the user can, for example, within the framework of the effect of the tool that is reasonable from a dental technology point of view and therefore proposed, continue to select one or even several regions of the 3D model, for which the effect of the tool is to be applied and thus, customize the 3D model. These selected regions can be at a distance to one another, adjoin each other or overlap. The regions may correspond to the identified regions in full or in part. The acceptance of the proposal in part then allows for applying the tool to one or several selected regions. The partial acceptance furthermore does allow for not only a local limitation of the proposed effect of the tool but also a limitation or influence with respect to the proposed strength of the effect. In this way, the effect can be weakened or strengthened using a strength factor. The strength factor can, for instance, be specified or selected by the user in percent or fractions, wherein different strength factors can be selected for different subregions.

In this way, partial effects both with respect to the local extent and with respect to the strength can be easily obtained and also accumulated or undone individually.

Preferably, a transition region is defined around the selected region, wherein the 3D model is adapted to the proposal model weighted in the transition region step-by-step by the strength factor.

By defining the transition region, a soft and/or smooth transition is, for example, possible between regions which are changed and unchanged with respect to the 3D model. The steps of the transition can be selected arbitrarily small and/or within the framework of the resolution of the 3D model in order to achieve as smooth a transition as possible. The steps may all be the same or may also be different across the transition region in accordance with another function so that the transition regions has, for example, a linear, exponential, parabolic or any other progression. The transition region and/or the type of the steps can be determined automatically by an arithmetic unit or by the user.

Preferably, the proposal model is displayed transparently or semi-transparently in the combined presentation. In this way, the user can perceive both the 3D model and the proposal at the same time and estimate the effect of the tool especially well.

Preferably, regions, in which the proposal model is covered by the 3D model in the combined presentation, are identified automatically and displayed on the 3D model.

If the 3D model is displayed opaquely, it is possible that the proposal model is completely or at least in places covered by the 3D model. The presentation of these regions on the 3D model, by marking them in color for example, allows a user to still perceive these regions or to estimate the effect of the tool in this region as well.

Preferably, a distance between the proposal model and the 3D model is displayed using a color coding of the proposal model.

A color coding of the distance simplifies estimating the effect of the tool.

Preferably, the result model and the 3D model are displayed alternately.

This allows the user to compare the effect of the tool selected by him with the original 3D model and to verify it.

Preferably, the at least one selected region is selected using an input device.

An input device allows for an easy selection process. For example, using a computer mouse or similar and a pointer that is displayed and movable by the computer mouse, a region can be selected and/or moved and/or deformed. Or, using a computer mouse or similar, a dot-shaped or circular pointer, for example, can be moved over the desired region to select it, just like a marker or pencil.

Preferably, a mark, which can be moved and selected using an input device, is displayed on the displayed 3D model for selecting a region.

The changing or moving of a mark on the 3D model allows for easy selection of subregions.

Preferably, a region of the proposal model, which corresponds to the selected region captured by the mark, is displayed opaquely and the selected region of the 3D model is transparently displayed or not displayed at all.

In this way, the effect of the tool in the selected region or the effect of the selection can be perceived directly and easily. This allows simple and quick verification.

Preferably, at least one line is defined and/or changed on the displayed 3D model using an input device.

Using one or several lines, the boundaries of regions to be selected can be marked. For example, the lines can be drawn on the 3D model free-hand using the input device. Or straight or even curved lines can be selected, positioned, combined and/or changed using the input device.

Preferably, at least one characteristic subregion of the 3D model is automatically identified and displayed and can be changed and/or selected using an input device.

Some objects and associated 3D models have characteristic regions. For example, teeth have very typical shapes, such as the cusps of molar teeth. The automatic identification of such characteristic structures simplifies the editing of the 3D model.

Preferably, the different regions are identified by means of averaged normal vectors.

As the shape of a tooth is composed at least approximately of several at least essentially flat surfaces, the normal vector can be used to identify regions with different orientations.

For this purpose, a normal vector, i.e. an averaged orthogonal direction, can be determined, for example, for each point of the 3D model. By means of the normal vectors, either regions as large as possible of points with a similarly oriented normal vector can be combined and/or each point can be assigned in accordance with the orientation of its normal vector to one of the expected directions, such as buccal, mesial, occlusal, distal etc. and thus to the appropriate group or surface.

Preferably, cusps and/or fissures are automatically identified as characteristic subregions within an occlusal surface.

Cusps and fissures constitute structures which are typical and very characteristic to occlusal surfaces. Especially in the use of tools on occlusal surfaces, it can be desirable to not change the entire surface uniformly but to only affect the cusps, for example, and leave the fissures as unchanged as possible.

Preferably, the cusps and/or fissures are identified by means of the curvature of the occlusal surface.

The curvature is characteristic for these structures and therefore a simple means for identifying cusps and fissures. A fissure has a negative curvature, for example, whereas a cusp has a positive curvature. For example, in order to identify a fissure, contiguous regions as large as possible of points with negative curvature are therefore identified and combined.

Preferably, the tool (T1, T2, T3) affects identified cusps and fissures differently.

In this way, it can be ensured that the characteristic shapes of the dental object, for example, the fissures, are preferably retained.

The tool T1, T2, T3) preferably takes into account neighboring teeth or adjacent restorations and/or opposite teeth or restorations and/or an emergence profile from at least one 3D data set.

Considering the surrounding structures is particularly important for editing dental objects. These surrounding structures may, for example, be available in the form of additional 3D data sets.

Thus, tools can bring about an approximation or adaptation to neighboring structures, such as neighboring teeth, or contact surfaces with opposing teeth or an adjustment of the size. A desired emergence profile can, for example, also be available for the dental object and the 3D model can be adapted to it. An adaptation to an emergence line of neighboring and/or opposite teeth is also possible.

BRIEF DESCRIPTION OF THE DRAWINGS

The method according to the invention is explained in reference to the drawing. In the drawing.

DETAILED DESCRIPTION OF THE INVENTION

Figure 1:
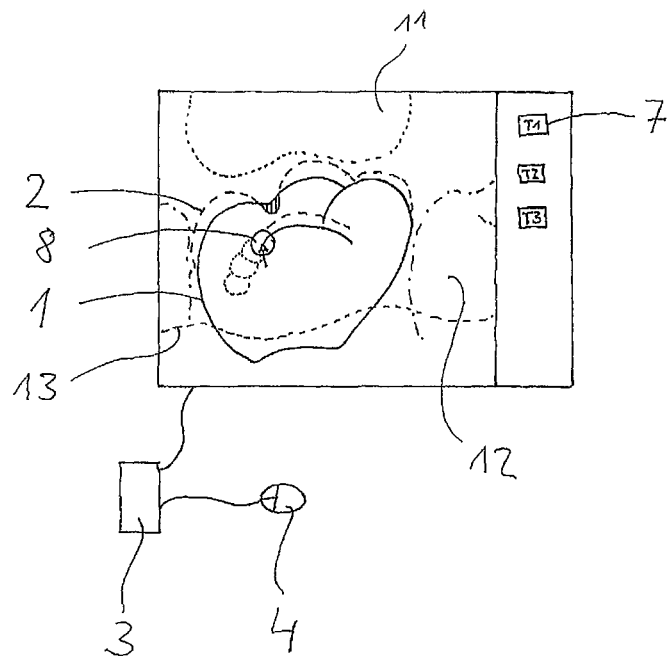
FIG. 1 shows a combined presentation of a 3D model and a proposal model.

FIG. 1 shows a combined presentation of a 3D model 1 of a molar tooth and a proposal model 2. The proposal model 2 is computed, for example, from the 3D model 1 using an arithmetic unit 3, for which the user selects a tool T1, T2, T3 to be applied to the 3D model 1. The selection of the tool T1, T2, T3 can, for example, be performed using a displayed selection button 7 and an input device 4, for example, a computer mouse. The tool T1, T2, T3 works pixel-by-pixel, for example, so that each pixel of the 3D model 1 corresponds to a pixel of the proposal model 2.

A tool T1, T2, T3 can, for example, effect an enlargement of the 3D model or an adaptation to a neighboring tooth. Tools T1, T2, T3 may also be provided for creating points of contacts to opposite teeth or for adjusting the progression of the lateral surfaces of a tooth to change and/or adapt the gingiva line, i.e. to obtain a desired emergence profile. For this purpose, these tools T1, T2, T3 can, for example, also draw on 3D datasets of one or several opposite teeth or restorations 11, one or both neighboring teeth or restorations 12 or an emergence profile 13.

In order to identify the 3D model 1 and the proposal model 2 well, the 3D model 1 may, for example, be opaquely displayed and the proposal model 2 transparently or semi-transparently. In order to assess the proposal model 2 well, the distance between the proposal model 2 and the 3D model 1 can, for example, be displayed by means of a color coding of the proposal model 2.

If the proposal model 2 is covered by the 3D model 1 in part or in full in the combined presentation, the regions and/or pixels of the 3D model 1, corresponding to the covered part of the proposal model 2, can be marked in color as indicated by the shaded region in FIG. 1.

However, it is also possible to display the concerned regions of the 3D model 1 transparently and the corresponding regions of the proposal model 2 opaquely. With such a presentation, there is, however, the risk that it can no longer be recognized clearly as to which displayed regions belong to which model. Nevertheless, this can be eliminated, for example, by a clear color separation by displaying one model, for example, in shades of red and the other model in shades of green.

Figure 2:
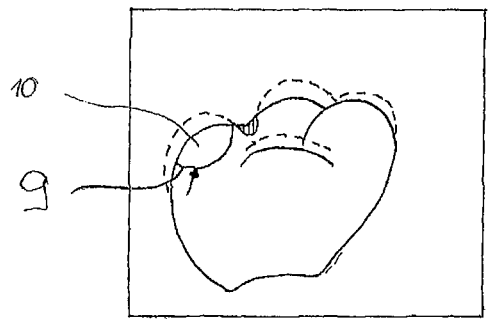
FIG. 2 shows the use of a selection tool.

Accepting the proposal model 2 or accepting portions thereof can be done, for example, using the input device 4. With the input device 4, the whole 3D model 1 can be selected, for example, by clicking or entering. If the tool T1, T2, T3 is only to affect subregions of the 3D model 1, this can be brought about, for example, by marking the then selected regions 10 using a mark 8 that is movable across the regions 10, as indicated in FIG. 1, or by limiting a selected region 10 using lines 9 that can be drawn, moved, changed and/or merged on the 3D model 1 using the input device 4. Selecting a region 10 using lines 9 is shown by the example in FIG. 2.

Figure 3:
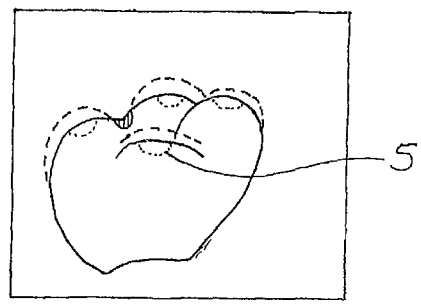
FIG. 3 shows the automatic selection of characteristic subregions.

The selecting of a region 10 can also be performed by selecting identified structures. The arithmetic unit 3 can determine characteristic subregions 5, such as cusps of an occlusal surface, which then can be, for example, as shown in FIG. 3, displayed by a boundary line, in this case a dotted line, and selected and/or changed using the input device 4, for example, enlarged and defined as selected region 10. Cusps and fissures of an occlusal surface of a tooth can, for example, be found using the curvature of the 3D model. While the 3D model has a more positive curvature in the region of the cusps, a more negative curvature is present in the region of a fissure.

Accepting the proposal can also occur in full or in part with respect to the form or strength of the effect. Using a strength factor S, for example, the effect of the tool T1, T2, T3 can be weakened or strengthened, for example, by not adjusting the 3D dataset to the proposal, or replacing the 3D dataset with the proposal, in full but only in part. The strength factor S can be selected or entered, for example by a user in percent or fractions. If the user selects a strength factor of 50% for a selected region 10, for example, the 3D model 1 is then adjusted to the proposal in the selected region 10 by 50%. This can, for example, occur pixel-by-pixel so that, for a result model 6, each pixel in the selected region 10 is set to a position that is at half the distance between the two models.

Figure 4:
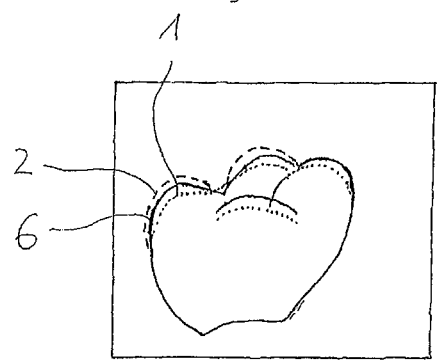
FIG. 4 shows a result model in a combined presentation with the proposal model.

In FIG. 4, a sample result model 6 is shown, which was obtained by accepting the proposal model 2 in two subregions with a respectively different strength factor S. The result model 5 is shown with a solid line, whereas the proposal model 2 is shown with a dashed line and the 3D model 1 with a dotted line. In the region of the two frontal cusps, a first selected region 10, the proposal was accepted at the full effect, i.e. at 100%. In the region of the two back cusps, a second selected region 10, the proposal was accepted only in part, i.e. at approx. 50%. Around the two selected regions 10, a transition region was, for example, automatically defined and a smooth transition between the regions unchanged with respect to the 3D model 1 and the two selected regions 10 was achieved.

In order to verify the results, the result model 6 can, for example, be displayed alternately with the 3D model 1 to allow for comparison.

Figure 5:
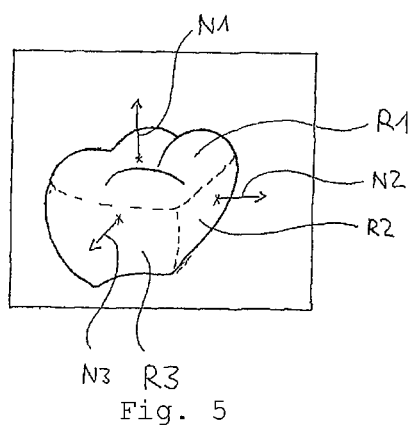
FIG. 5 shows a 3D model with automatically identified regions.

In order to ensure that the tool T1, T2, T3 only affects the 3D model 1 to a degree that is reasonable from a dental technology point of view, the effect of the tool T1, T2, T3 varies for different regions R1, R2, R3 of the 3D model. For this purpose, different regions R1, R2, R3 of the 3D model are automatically identified, an occlusal surface R1, a mesial surface R2 and a lingual surface R3, for example, as sketched in FIG. 5. This may, for example, occur by means of a normal vector N1, N2, N3, by determining a normal vector N1, N2, N3 for each point of the 3D model and combining regions with normal vectors N1, N2, N3 at more or less the same direction into a region R1, R2, R3. Each point can also be assigned, based on the direction of its normal vector N1, N2, N3, to a certain orientation, such as occlusal, mesial, lingual, etc. and thus, to the corresponding region R1, R2, R3.

Cusps and/or fissures of a chewing surface or occlusal surface can also be automatically identified as regions R1, R2, R3 so that the effect of a tool can also be varied automatically with respect to these structures. As described above, identification is possible in the region of the occlusal surface, for example, by means of the curvature of the 3D model.

Depending on the tool, the effect can be limited to one or several identified regions R1, R2, R3, for example, or even to a central area of the region R1, R2, R3.

LIST OF REFERENCE SYMBOLS 1 3D model
2 Proposal model
3 Arithmetic unit
4 Input device 5 Characteristic subregion
6 Result model
7 Selection button
8 Mark
9 Line
10 Selected region
11 Opposite tooth
12 Neighboring tooth
13 Emergence profile
N1 Normal vector
N2 Normal vector
N3 Normal vector
R1 Region
R2 Region
R3 Region
S Strength factor
T1 Tool
T2 Tool
T3 Tool

The invention claimed is:

1. A computer assisted method for the editing of a digital 3D model of a dental object using one or more digital tools comprising:
producing a 3D model using a dental camera;
identifying one or more different regions of the 3D model by determining a normal vector for each point of the 3D model and combining regions having normal vectors in substantially the same direction into the one or more different regions;
selecting at least one digital tool,
producing a proposal model, different from the 3D model, by applying the at least one digital tool to the 3D model;
computing an effect of the at least one digital tool for the 3D model, wherein the at least one digital tool corresponds each point of the 3D model to a point of the proposal model by a direction determined by the normal vector and by a distance computed by an approximation or adaptation to neighboring structures that are in the form of 3D data sets, wherein at least one region of the one or more different regions of the 3D model corresponds at least in part to an occlusal or incisal or labial or buccal or distal or mesial or lingual or palatal surface of the dental object, and wherein the at least one digital tool affects the different regions of the one or more different regions differently while retaining the characteristic shapes of the dental object,
responsive to selecting at least a region of the 3D model, providing at least the region of the 3D model as at least one of one or more selected regions;
responsive to selecting at least a subregion of the 3D model, providing at least the subregion of the 3D model as at least one of the one or more selected regions;
responsive to selecting the 3D model, providing the 3D model as the one or more selected regions,
automatically producing a result model from the 3D model, the proposal model and the one or more selected regions by:
automatically replacing, responsive to accepting the proposal model in full in one or more corresponding regions corresponding to a first group of the one or more selected regions, the first group of the one or more selected regions with the one or more corresponding regions of the proposal model;
automatically setting, responsive to partially accepting the proposal model in one or more other corresponding regions corresponding to another group of the one or more selected regions, each point of a member region in the another group of the one or more selected regions to a positional distance between the two models, computed according to a strength factor of the member region; and
displaying the result model.

2. The method according to claim 1, wherein the proposal model is displayed transparently in the combined presentation.

3. The method according to claim 1, wherein parts of the 3D model cover parts of the proposal model in the combined presentation.

4. The method according to claim 1, wherein a distance between the proposal model and the 3D model is displayed using a color coding of the proposal model.

5. The method according to claim 1, wherein the result model and the 3D model are displayed alternately.

6. The method according to claim 1, wherein the one or more selected region is/are selected using an input device.

7. The method according to claim 1, wherein a mark, which can be moved and selected using an input device, is displayed on the displayed 3D model for selecting a region.

8. The method according to claim 7, wherein a region of the proposal model , which corresponds to the selected region and is captured by the mark, is displayed opaquely and the selected region of the 3D model is displayed transparently or not displayed at all.

9. The method according to claim 1, wherein one or more lines are drawn, moved, changed and/or merged on the 3D model and the one or snore lines are defined and/or changed using an input device.

10. The method according to claim 1, wherein at least one characteristic subregion of the 3D model is automatically identified and displayed and can be changed and/or selected using an input device.

11. The method according to claim 1, wherein the different regions are identified by means of averaged normal vectors.

12. The method according to claim 1, wherein cusps and/or fissures are automatically identified as characteristic subregions within an occlusal surface.

13. The method according to claim 12, wherein the cusps and/or fissures are identified by means of the curvature of the occlusal surface.

14. The method according to claim 12, wherein the at least one digital tool affects identified cusps and fissures differently.

15. Method according to claim 1, wherein the at least one digital tool takes into account neighboring teeth or restorations and/or opposite teeth or restorations and/or an emergence profile from at least one 3D data set.

16. The method according to claim 1, wherein the one or more selected regions is the 3D model and the result model is the proposal model.

17. The method according to claim 1, wherein the one or more other corresponding regions corresponding to the another group of the one or more selected regions is a plurality of other corresponding regions and wherein the result model is produced by automatically setting, responsive to partially accepting the proposal model in the plurality of other corresponding regions, each point of the member region in the another group of the one or more selected regions to the positional distance between the two models, computed according to the strength factor of the member region.

18. A computer assisted method for the editing of a digital 3D model of a dental object using one or more digital tools comprising:

selecting at least one digital tool and computing an effect of the at least one digital tool for the 3D model;

identifying one or more different regions of the 3D model by determining a normal vector for each point of the 3D model and combining regions having normal vectors in substantially the same direction into the one or more different regions, wherein at least one region of the one or more different regions of the 3D model corresponds at least in part to an occlusal or incisal or labial or buccal or distal or mesial or lingual or palatal surface of the dental object, and wherein the at least one digital tool affects the different regions of the one or more different regions differently while retaining the characteristic shapes of the dental object, providing the effect computed for the 3D model as a proposal model, the proposal model is different from the 3D model, and displaying the proposal model together with the 3D model, with wherein the at least one digital tool corresponding each point of the 3D model to a point of the proposal model by a direction determined by the normal vector and by a distance computed by an approximation or adaptation to neighboring structures that are in the form of 3D data sets;

responsive to selecting at least a region of the 3D model, providing at least the region of the 3D model as at least one of one or more selected regions;

responsive to selecting at least a subregion of the 3D model providing at least the subregion of the 3D model as at least one of the one or more selected regions;

responsive to selecting the 3D model, providing the 3D model as the one or more selected regions, automatically producing a result model from the 3D model, the proposal model and the one or more selected regions by:

automatically replacing, responsive to accepting the proposal model in full in one or more corresponding regions corresponding to a first group of the one or more selected regions, the first group of the one or more selected regions with the one or more corresponding regions of the proposal model;

automatically setting, responsive to partially accepting the proposal model in one or more other corresponding regions corresponding to another group of the one or more selected regions, each point of a member region in the another group of the one or more selected re ions to a positional distance between the two models, computed according to a strength factor of the member region; and displaying the result model.

19. A non-transitory computer readable storage medium tangibly embodying a computer readable program code having computer readable instructions that, when executed, causes a processor to carry out a method of editing a digital 3D model of a dental object using one or more digital tools comprising, the method comprising:

producing a 3D model based on a dental camera;

identifying one or more different regions of the 3D model by determining a normal vector for each point of the 3D model and combining regions having normal vectors in substantially the same direction into the one or more: different regions;

selecting at least one digital tool, producing a proposal model, different from the 3D model, by applying the at least one digital tool to the 3D model;

computing an effect of the at least one digital tool for the 3D model, wherein the at least one digital tool corresponds each point of the 3D model to a point of the proposal model by a direction determined by the normal vector and by a distance computed by an approximation or adaptation to neighboring structures that are in the form of 3D data sets, wherein at least one region of the one or more different regions of the 3D model corresponds at least in part to an occlusal or incisal or labial or buccal or distal or mesial or lingual or palatal surface of the dental object, and wherein the at least one digital tool affects the different regions of the one or more different regions differently while retaining the characteristic shapes of the dental object, responsive to selecting at least a region of the 3D model, providing at least the region of the 3D model as at least one of one or more selected regions;

responsive to selecting at least a subregion of the 3D model, providing at least the subregion of the 3D model as at least one of the one or more selected regions;

responsive to selecting the 3D model, providing the 3D model as the one or more selected regions, automatically producing a result model from the 3D model, the proposal model and the one or more selected regions by:

automatically replacing, responsive to accepting the proposal model in full in one or more corresponding regions corresponding to a first group of the one or more selected regions, the first group of the one or more selected regions with the one or more corresponding regions of the proposal model;

automatically setting, responsive to partially accepting the proposal model in one or more other corresponding regions corresponding to another group of the one or more selected regions, each point of a member region in the another group of the one or more selected regions to a positional distance between the two models, computed according to a strength factor of the member region; and displaying the result model.

* * * * *